(12) United States Patent
Erdmann

(10) Patent No.: US 7,476,205 B2
(45) Date of Patent: Jan. 13, 2009

(54) APPARATUS FOR TREATMENT OF PATIENTS WHO SUFFER FROM LESIONS DISTRIBUTED ON THE SURFACE OF THEIR SKIN AND BODY COVER

(76) Inventor: Alfons Erdmann, Kantstrasse 7, D-60316 Frankfurt (DE)

( * ) Notice: Subject to any disclaimer, the term of this patent is extended or adjusted under 35 U.S.C. 154(b) by 226 days.

(21) Appl. No.: 11/584,053

(22) Filed: Oct. 20, 2006

(65) Prior Publication Data

US 2007/0060848 A1 Mar. 15, 2007

Related U.S. Application Data

(60) Provisional application No. 60/728,773, filed on Oct. 21, 2005.

(51) Int. Cl.
*A61H 1/00* (2006.01)
*A61F 13/00* (2006.01)
(52) U.S. Cl. .............. 601/6; 601/7; 601/11; 601/1
(58) Field of Classification Search .............. 601/6, 601/7, 11, 1
See application file for complete search history.

(56) References Cited

U.S. PATENT DOCUMENTS

| | | | |
|---|---|---|---|
| 4,382,441 A | 5/1983 | Svedman | 604/291 |
| 5,645,081 A | 7/1997 | Argenta et al. | 128/897 |
| 2005/0026125 A1* | 2/2005 | Toly | 434/262 |

FOREIGN PATENT DOCUMENTS

| | | |
|---|---|---|
| DE | 32 19 325 | 11/1983 |
| DE | 29 53 373 | 12/1989 |
| DE | 93 08 780 | 8/1993 |
| DE | 295 04 894 | 6/1995 |
| DE | 694 25 881 | 3/2001 |
| DE | 202 07 389 | 8/2002 |
| DE | 20 2004 017 052 | 6/2005 |
| EP | 1518524 | 3/2005 |
| WO | WO 9420041 | 9/1994 |
| WO | WO0185228 | 11/2001 |
| WO | WO0243634 | 6/2002 |
| WO | WO 03/018098 | 3/2003 |
| WO | WO03092620 | 11/2003 |
| WO | WO 2006 048 240 | 5/2006 |

OTHER PUBLICATIONS

English translation of claims 1-3 of DE 202 07 389.

* cited by examiner

*Primary Examiner*—Nikita Wells
(74) *Attorney, Agent, or Firm*—Davidson, Davidson & Kappel, LLC

(57) ABSTRACT

A device for treating patients who suffer from skin lesions distributed on their body surface. A body cover has one or more cover elements, the cover elements having a gastight layer and being flexible to fit to body parts in a tight manner. Advantageously at least in the areas with skin lesions there are provided open-pored sponge-like bodies on the side of the gastight layer facing the patient's body as well as connection ports for the exchange of fluids, especially for the generation of low pressure. By making at least one of the cover elements in the form of a tube, they are easy to handle and applicable to extensive lesions.

24 Claims, 3 Drawing Sheets

APPARATUS FOR TREATMENT OF PATIENTS WHO SUFFER FROM LESIONS DISTRIBUTED ON THE SURFACE OF THEIR SKIN AND BODY COVER

This claims priority to U.S. Provisional Patent Application No. 60/728,773, filed Oct. 21, 2005 and hereby incorporated by reference herein.

BACKGROUND

The present invention refers to the field of treatment of patients with heavy skin lesions, for example burns widely distributed on their skin surface.

The treatment of persons heavily injured from burns is currently carried out in different medical centres following a common standard according to the currently widely accepted opinion of medical researchers. In spite of a careful treatment and a long and expensive stay of the patients in medical centres there is a high grade of lethality especially with high grade burns or similar skin lesions covering big parts of a person's skin. As a result, there are also losses of grafts requiring additional surgeries. Changes of bandages are required frequently and have to be carried out under anaesthetic. They are very time consuming and expensive. Systemic infections are difficult to control and can not always be avoided.

From the prior art, vacuum treatment methods are known to treat such skin lesions which can improve the treatment, lead to a faster healing and success including lowering the costs of the treatment.

From PCT-application WO 03/0180 98 A2 there is known a system for treatment of patients using a sponge body which is put on a wound and where a gastight cover is applied in a gastight manner on the surface of the patient's body. The cover is connected with means for generating a vacuum.

By the sucking of air a vacuum is generated in the area of the lesion which boosts the healing and at the same time supports pressing the sponge body against the lesion.

The known system is not satisfying, as it allows only treatment of small and limited skin lesions because the tightening around the sponge body requires an area of healthy skin of a patient. It is very laborious to apply the cover in a gastight manner to a patient because the gastight layer of the cover has to be applied without crease. This is not easy because the foil used as a gastight layer is difficult to handle.

SUMMARY OF THE INVENTION

The present invention minimizes the above mentioned problems and provides a simple solution which can be handled easily. The apparatus has a body cover with one or more cover elements. The cover elements have a gastight layer and are flexible enough to fit to a body part of the patient. At least one of said cover elements is tube-like. The body cover has at least one lead-through for the exchange of fluids, especially for generating low pressure around the body of the patient.

Because of the tube-like formation, the cover element can be easily placed around a body part or the body of a patient wherein gastightning must be secured at the ends of the tube only. The type of gastightning at the end of the tube-like cover elements will be described more in detail below. By the lead-through the body of the patient can for example be exposed to vacuum which substantially improves the treatment, especially for patients suffering from burns. By such type of lead-through it is also possible to remove fluids, i.e. liquids or gases from the patients body by sucking or applying them to the patient's body. On the side of the cover elements facing the patient's body, there can be provided either one continuous open-pored sponge body, which can be fixed to the cover elements or single sponge bodies can be put on in the areas of skin lesions before the body cover is applied. Thereby, a distance between the gastight layer and the skin surface of the patient is secured, air or other fluids can be sucked through the sponge body and especially vacuum can be generated through such a sponge body. At the same time the sponge body is pressed against the surface of the patient's body by atmospheric air pressure.

An open-pored sponge-like material shall mean materials that are not gastight and can be put on the body surface. They can be soft or hard, flexible or stiff, as long as they can be pressed against the body surface and as long as they can be passed by fluids.

In the case of a body cover comprising more than one cover element, they or at least some of the cover elements can be connected in a gastight manner, for example by gastight zippers or adhesive flanges.

On one side, the body cover can be comfortably applied by covering single extremities with single tube-like elements and, if necessary, connecting the tube-like elements. The single tube-like cover elements can have different sizes to facilitate putting together a body cover fitting to the size of the patient. Standard cover elements can be held on stock enabling to fit a suit-like body cover to an individual patient. On the other side, complete suits can be held on stock wherein the single cover elements can be separated at the connecting ends to put them on the patient and wherein the connecting elements can thereafter be connected in a gastight manner.

Also, there can be provided cover elements with, at one of the ends, a circular collar for gastight connection with the skin surface of the patient. Such a collar can for example be rubber-like and elastic, adhesive or connectible by chemical or physical adsorption.

Such type of tube-like cover elements can be applied to the extremity one by one if for example there is only one separate skin lesion and in this case on both sides of the skin lesion the extremity can be connected in a gastight manner with the cover element by a collar. The space between the collars is thereby closed in a gastight manner and vacuum can be applied to the space. On the other side, the cover elements can also be connected to other cover elements by a flange, if for example one half of the patient's body is injured, thereby covering the injured half of the body while on the other side of the patient's body the extremities remain uncovered and the suit being gastightly closed on the upper arm or femoral by a collar.

One or more of the cover elements can also provide sack-like ends that can be put around the extremities of the patient. Such type of sack-like cover element can for example be formed as a hood for the head of the patient. In this case a flexible tube should be fed-through to enable breathing of the patient. There can also be provided feed-throughs for probes, for example a stomach tube or a tube to feed the patient with food or other substances, or a probe for carrying out measurements on the body of the patient. The hood can advantageously be removable keeping the other cover elements gastightly fixed to the patient.

At one or more points of the cover elements there can be provided connection-ports to connect them with means for generating low pressure. Those connection-ports can be simple closable or self-closing valves. In addition, there can be provided valves for the application or removal of an easy to dose fluid, which allow to remove body liquids and on the other side application of antiseptic or pharmacologically active liquids in a dosed manner. Fluids that are applied can also be removed by sucking by the means for generating low pressure. In this way application of certain fluids to the patient's body can be well controlled.

For the constant application or removal of fluids i.e. liquids or gases to or from the whole body cover, a ramified system of tubes can be provided on the outside of the body cover. In this way liquids can be applied or removed at different points and also, low pressure can be evenly distributed on the body surface. If there is provided a system for applying or removing fluids on the inner side of the body cover, this should consist of none collapsible cavities as the respective tubes are submitted to the pressure from the gastight layer of the body cover. Such a system of tubes can advantageously be integrated into the body cover itself wherein connection-ports for the tubes have to be provided in the single cover elements.

The gastight layer of the cover elements can for example include foamed elastomer material as for example known under the trade mark neoprene. The layer can also be made of foil-type flexible materials, especially polyethylene or polyvinylhloride.

Especially advantageous can be to make the cover elements optically transparent to enable observation of the healing process from the outside.

Instead of this or additionally, inspection-openings can be provided at the cover elements that can be opened or closed for example by a gastight zipper.

It can also be advantageous to provide between the body surface of the patient and the sponge body a permeable layer which separates and protects the body of the patient from the influence of the sponge body. In some cases it has turned out to be advantageous to provide a silicone tissue as a layer.

The invention also refers to an apparatus for treatment of patients suffering from skin lesions with at least one cover element from a flexible material with a gastight layer with at least one open-pored sponge body on the side of the gastight layer facing the patient's body and with one gastight closure of the cavity containing the sponge body, wherein the cover elements have at a first point one connection-port connectible with means for generating low pressure and at a second point, distant from the first point, a connection-port connectible with means for applying a fluid.

During the practical application the first connection-port is for example connected to a vacuum pump serving as means for generating low pressure and said second connection-port can be connected with a liquid reservoir, for example an infusion. Depending on the condition of the patient and the extension of the injuries, also the body temperature of the patient can be controlled. For this purpose, an apparatus for control of the temperature of the fluid applied can be provided. In this way the body of the patient can be cooled or warmed up. To enable a respective control, on the inner side of the body cover sensors for measuring temperature can be provided. In this case the invention also comprises an apparatus for controlling the application of fluids and their temperature and which uses the data of the temperature sensors. In addition, the sucking of fluids is being controlled for example to check if there are leaks in the body cover.

It is possible to exactly measure the quantity of the liquid applied and the quantity of the liquid removed from the body and to compare the two quantities to calculate differences to analyse the balance of body liquids of the patient which delivers important data concerning the health state of the patient.

The present invention not only refers to the apparatus described above but also to cover elements or to a body cover put together from cover elements for such an apparatus or to a suit for a patient put together from cover elements or a part of a suit put together.

BRIEF DESCRIPTION OF THE DRAWINGS

The present invention will below be shown in a drawing by examples and will be described with reference to the figures, whereby.

DETAILED DESCRIPTION

Figure 1:
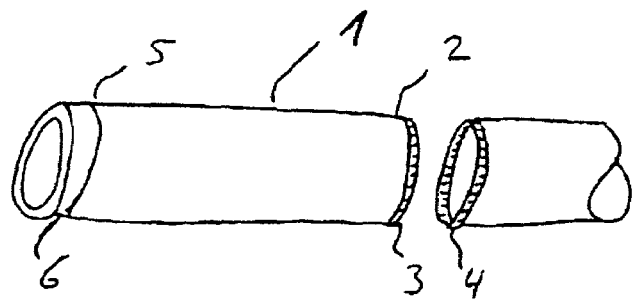
FIG. 1 schematically shows two tube-like cover elements.

FIG. 1 schematically shows a first cover element 1 in the form of a tube, into which for example an arm or a leg of a patient can be introduced. Larger tubes are provided for the body of the patient. In the area of the first end 2 of the cover element 1 a part of a zipper 3 is shown, which acts together with a further part 4 of the zipper being closable in a gastight manner by zipper 3.

At the second end 5 being positioned distant from said first end 2 of the cover element, there is provided an elastic flange with an adhesive layer that can be applied to an extremity of the patient in a gastight manner.

Figure 2:
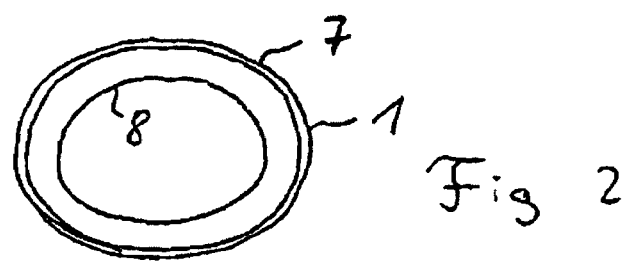
FIG. 2 schematically shows a cover element in a cross-sectional view.

In FIG. 2 there is shown a tube-like cover element 1 in a cross-sectional view. The cover element 1 has, on its outside a gastight layer 7 which is for example made of neoprene, polyvinylchloride or polyethylene but can also be made of other flexible and gastight materials. On the inner side of the gastight layer 7 there is an open-pored sponge body 8 continuously distributed. This sponge body 8 is permeable to fluids enabling that air and liquids can be sucked through it and that a vacuum in the area of the skin lesions covered can be applied.

Figure 5:
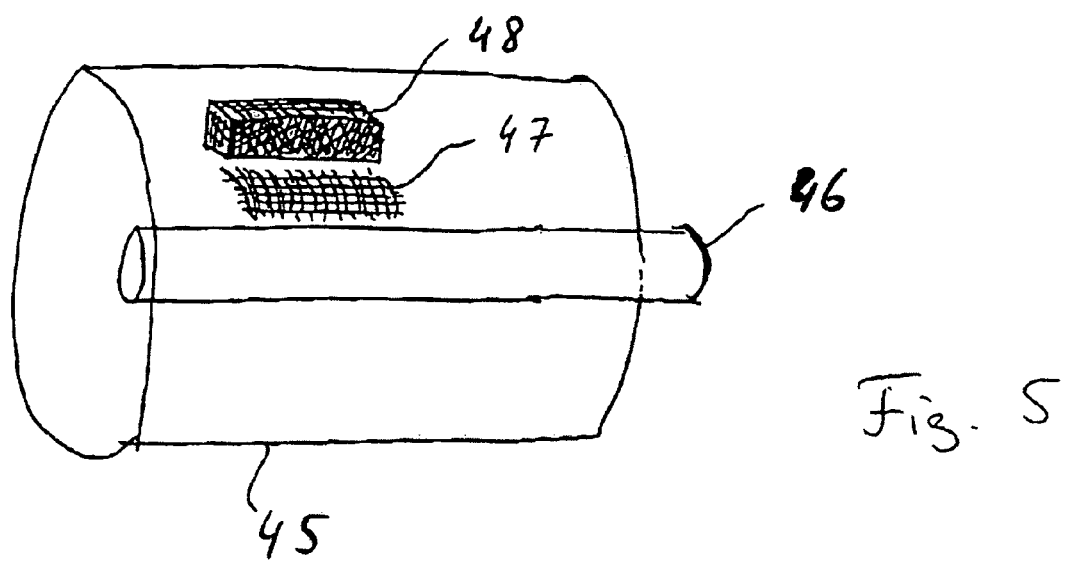
FIG. 5 shows schematically a sponge body, a cover element and a silicone tissue.

The sponge material 8 is not necessarily distributed on the whole inner side of the cover elements but can also only be provided in the area of the skin lesions as is shown more in detail in FIG. 5. In this case there is no continuous layer of open-pored sponge-like material on the inner side of the gastight layer 7.

Figure 3:
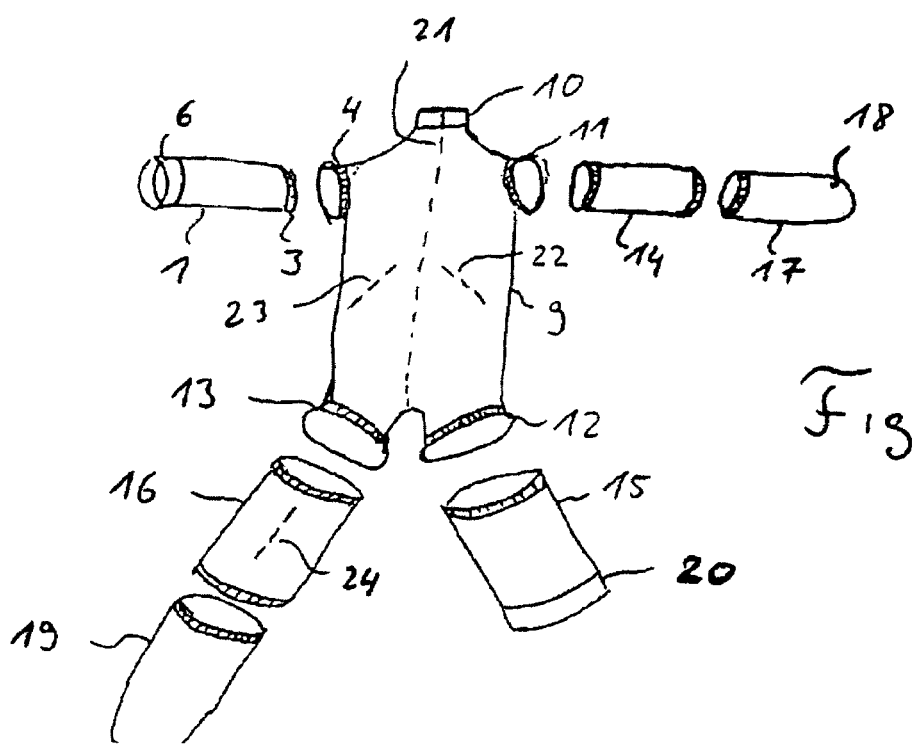
FIG. 3 shows a schematic suit put together from cover elements.

FIG. 3 schematically shows that a vacuum suit for a patient can be put together from cover elements. The drawing additionally shows that a first cover element 1 on one end has a flange 6 and on the other hand a part 3 of a zipper. The part 3 of the zipper acts together with an other part 4 of a zipper which is fixed to a cover element 9 for the body of the patient. The cover element for the body has a gastight flange 10 for tightening at the neck of the patient, said flange being rubber-like and elastic. Where the extremities are connected to the patient's body, openings are provided with zipper-parts 11, 12, 13 for the connection of respective tube-like cover elements 14, 15, 16. Cover element 14 has another flange which allows for the connection to another cover element 17 which on its other end 18 provides a sack-like closing covering the hand of the patient.

A similar sack-like closure is provided at the cover element 19 covering the foot of the patient. The cover element 15 on one of its ends provides a zipper part for connection to the body cover element 9, on its other end it provides a flange 20 for the gastight closure at the femoral of the patient.

Cover elements like those shown in FIG. 3 can be held on stock for the treatment of patients wherein different sizes for different body sizes of the patients can be provided. Respective suits can also be pre-configured and held on stock.

The cover element 9 provided for the body also shows along the dotted line 21 a zipper which is gastight and serves for inserting the patient's body. Additionally there are provided inspection openings 22, 23, 24 also comprising zippers and being showed as dotted lines. It goes by itself that additional inspection openings can be provided, that are not shown in the figure to keep the figure concise.

Figure 4:
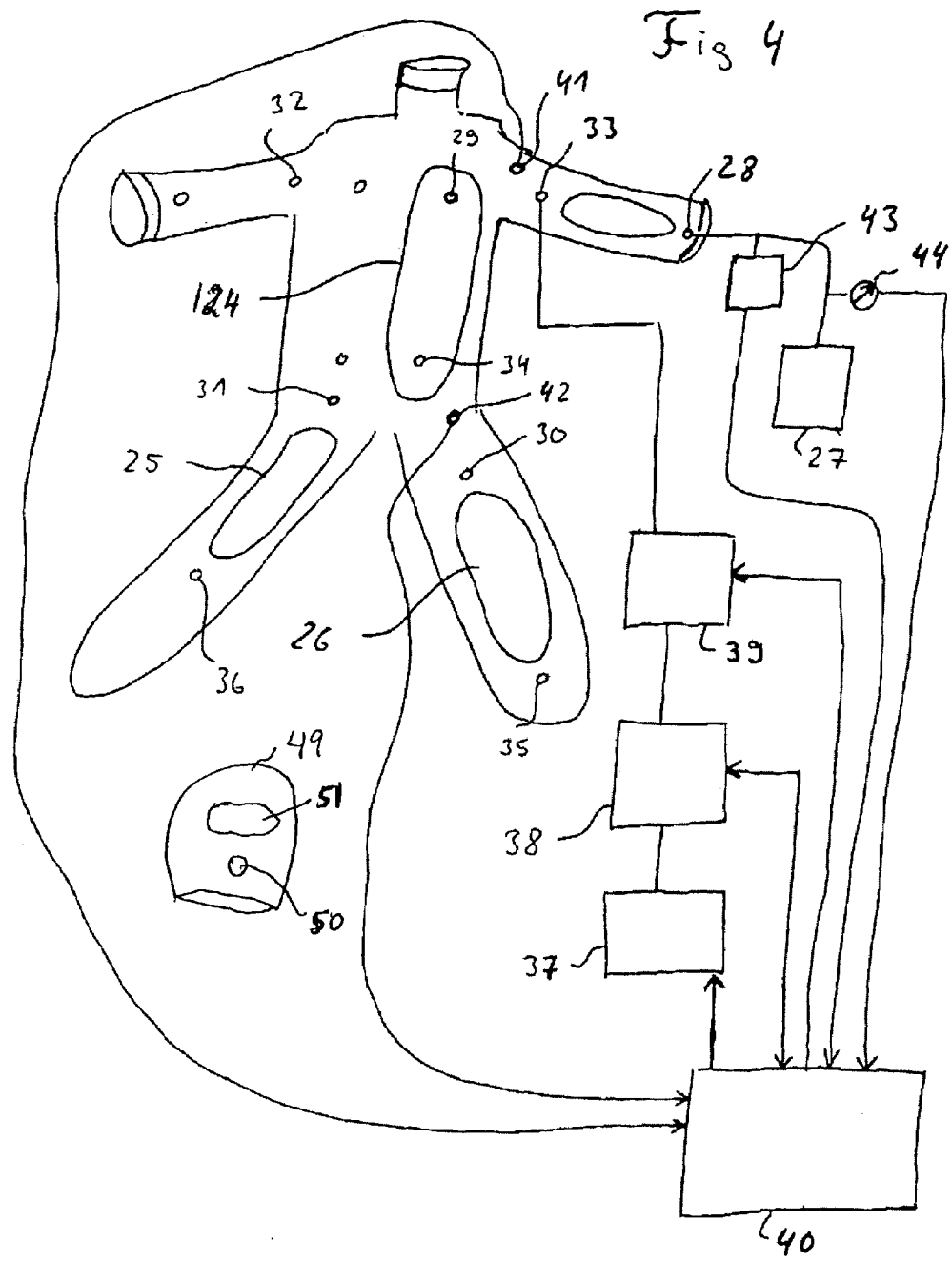
FIG. 4 shows an apparatus according to the invention with respective connection-ports an accessories.

FIG. 4 shows a vacuum suit similar to that shown in FIG. 3 wherein additional accessories are shown which can be part of the apparatus.

The suit shown in FIG. 4 comprises only a gastight layer wherein before inserting the patient's body into the suit, sponge bodies 124, 25, 26 in the area of the skin lesions of the patient's body are inserted. Distributed over the suit are connection-ports for connecting a vacuum pump 27. The connection-ports are symbolized by 28, 29, 30, 31, 32 wherein not necessarily all of them are connected to the vacuum pump. As a matter of example the connection of the connection-port 28 to a vacuum pump 27 is shown.

In addition the connection-ports for applying fluids are shown as numbers 33, 34, 35, 36. As a matter of example only the connection-port 33 is connected to an apparatus 37 for applying a fluid. Between the apparatus 37 and the connection-port 33 there is an apparatus 38 for control of the quantity of fluid and an apparatus 39 for control of the temperature of the fluid. Both apparatuses 38, 39 are controlled by a steering or distribution unit 40 which receives data about the temperature of the patient's body from sensors 41, 42 which are shown in the figure only as examples. The steering unit 40 also receives data from the dosing unit 38 about the quantity of liquid applied and data from the apparatus 43 serving to collect the body secret concerning the quantity the liquid sucked in. The steering unit 40 on one side can control the body temperature of the patient and on the other side can carry out calculations about the balance of liquids applied and removed to get information about the body liquid balance of the patient.

The steering unit 40 is also connected with a pressure measuring unit 44 which measures the low pressure generated by the pump 27 to get information for example about possible leaks in the body cover.

FIG. 4 also shows an additional cover element in the form of a hood 49 with a transparent eye-part 51 and a breathing tube 50.

FIG. 5 schematically shows a tube-like cover element 45 which only comprises a gastight layer and which is applied on an extremity 46 only schematically symbolized which can for example be the arm of a patient, inserting between said gastight layer and the extremity a silicone tissue 47 and an open-pored sponge body 48. The respective gas tightenings are not shown in FIG. 5 but can be seen in the other figures.

Generally, it can be said that the shown examples of a body cover for a patient can improve the healing process by the controlled application of a low pressure with the insertion of open-pored sponge bodies also for patients with extensive skin lesions, especially burns, and that costs and time for treating a patient can be spared by improving and facilitating the handling of such a body cover.

The different measures shown can be applied separately or combined with each other in various configurations.

What is claimed is:

1. An apparatus for treating patients suffering from skin lesions distributed on the body surface, comprising:
    a body cover with at least one cover element, the cover element including a gastight layer and being flexible to fit to a body part of a patient, the body cover having at least one lead-through enabling the exchange of a fluid, wherein at least one the cover elements is formed as a tube.

2. The apparatus according to claim 1, further comprising open-pored sponge bodies at least in the areas of skin lesions on a side of the gastight layer facing a body of the patient.

3. The apparatus according to claim 1 wherein the at least one cover element includes two cover elements connected to each other in a gas-tight manner.

4. The apparatus according to claim 1 wherein the at least one cover element includes two cover elements connected to each other by a gastight zipper.

5. The apparatus according to claim 1 wherein the cover element has a circular collar for tightening on the body surface of the patient at one end.

6. The apparatus according to claim 5 wherein said circular collar is rubber-like and elastic.

7. The apparatus according to claim 5 wherein the circular collar is adhesive or carries an adhesive or is formed of a material generating adhesive forces to the surface of a body of the patient.

8. The apparatus according to claim 1 wherein the cover element has a sack-like closure for covering the end of an extremity or forming of a hood.

9. The apparatus according to claim 8 wherein the cover element formed as a hood has a lead-through for a breathing-tube, a probe or a catheter.

10. The apparatus according to claim 1 wherein the cover element at one or more positions has a connection port provided for the connection with a low pressure generator.

11. The apparatus according to claim 1 wherein at various points of the body cover includes valves for dose application or removal of fluids.

12. The apparatus according to claim 1 wherein the cover element has a connection port for a catheter.

13. The apparatus according to claim 1 further comprising a distributed system of tubes on an outside of the body cover for sucking the fluid at several connection ports of the body cover or serving for generation of low pressure in an area of the body cover.

14. The apparatus according to claim 1 further comprising a system of non-collapsible tubes for communication of the fluid on a side of the gastight layer facing a body of the patient.

15. The apparatus according to claim 1 wherein the gastight layer includes a foamed elastomer material.

16. The apparatus according to claim 1 wherein the gastight layer includes a foil-type flexible material of polyethylene or polyvinylchloride.

17. The apparatus according to claim 1 wherein the cover element is at least partially optically transparent.

18. The apparatus according to claim 1 wherein the cover element has an inspection opening closeable by a gastight zipper.

19. The apparatus as recited in claim 1 wherein the fluid generates a low pressure.

20. An apparatus for treating patients who suffer from skin lesions distributed on their body surface comprising:

at least one cover element made of a flexible material, the cover element including:

a gastight layer;

an open-pored sponge body on the side of the gastight layer facing a body of a patient with a gastight sealing of the cover element;

the cover element at a first position having a first connection port connectible with a low pressure generator and the cover element at a second position at a distance from the first position having a second connection port connectible with a fluid supply.

21. The apparatus according to claim 20 wherein the fluid supply is a dose infusion device.

22. The apparatus according to claim 20 further comprising a temperature controller for the fluid supplied by the fluid supply.

23. The apparatus according to claim 20 further comprising temperature sensors for measuring a local body temperature on a side of the gastight layer facing the body.

24. A body cover comprising the apparatus according to claim 1.

* * * * *